United States Patent
Prencipe et al.

(10) Patent No.: US 9,610,148 B2
(45) Date of Patent: *Apr. 4, 2017

(54) APPLICATOR AND METHOD FOR APPLYING A TOOTH WHITENING COMPOSITION

(71) Applicant: COLGATE-PALMOLIVE COMPANY, New York, NY (US)

(72) Inventors: Michael Prencipe, Princeton Junction, NJ (US); Suman Chopra, Monroe, NJ (US); Joseph Thomas Norris, Cumming, GA (US); Adolfo Serrano, San Jose (CR)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/460,113

(22) Filed: Aug. 14, 2014

(65) Prior Publication Data

US 2014/0356807 A1 Dec. 4, 2014

Related U.S. Application Data

(60) Division of application No. 11/403,732, filed on Apr. 13, 2006, now Pat. No. 8,815,216, which is a continuation of application No. PCT/US2004/033502, filed on Oct. 12, 2004.

(60) Provisional application No. 60/511,020, filed on Oct. 14, 2003.

(51) Int. Cl.

| A45D 34/00 | (2006.01) |
|---|---|
| A45D 34/04 | (2006.01) |
| A61K 8/00 | (2006.01) |
| A61K 8/22 | (2006.01) |
| A61Q 11/00 | (2006.01) |
| A61C 19/06 | (2006.01) |
| A46B 9/02 | (2006.01) |
| A46B 11/00 | (2006.01) |
| A46B 17/04 | (2006.01) |
| A61C 3/00 | (2006.01) |
| A61K 8/81 | (2006.01) |

(52) U.S. Cl.
CPC ............ *A61C 19/066* (2013.01); *A46B 9/021* (2013.01); *A46B 11/0024* (2013.01); *A46B 11/0027* (2013.01); *A46B 17/04* (2013.01); *A61C 3/005* (2013.01); *A61C 19/063* (2013.01); *A61K 8/22* (2013.01); *A61K 8/8147* (2013.01); *A61Q 11/00* (2013.01); *A46B 2200/1046* (2013.01); *A46B 2200/20* (2013.01)

(58) Field of Classification Search
USPC ........................................ 401/171; 424/49, 53
See application file for complete search history.

(56) References Cited

U.S. PATENT DOCUMENTS

| 1,907,350 | A | 5/1933 | Fried |
|---|---|---|---|
| 3,376,110 | A | 4/1968 | Shiraeff et al. |
| 3,480,557 | A | 11/1969 | Shiraeff |
| 5,122,370 | A | 6/1992 | Merianos et al. |
| 5,292,502 | A | 3/1994 | Burke et al. |
| 5,320,442 | A | 6/1994 | Yanagisawa et al. |
| 5,611,687 | A | 3/1997 | Wagner et al. |
| 5,827,002 | A | 10/1998 | Nakajima |
| 6,096,328 | A | 8/2000 | Sagel et al. |
| 2003/0232310 | A1 | 12/2003 | Matthews et al. |
| 2005/0026107 | A1 | 2/2005 | Montgomery |

FOREIGN PATENT DOCUMENTS

| CN | 1368034 | 9/2002 |
|---|---|---|
| EP | 0 284244 | 3/1998 |
| WO | WO 01/34107 | 5/2001 |
| WO | WO 01/68045 | 9/2001 |
| WO | WO 02/41802 | 5/2002 |
| WO | WO 2004/112637 | 12/2004 |

OTHER PUBLICATIONS

State Intellectual Property Office of People's Republic of China Search Report issued in CN201110111493.2 mailed Jan. 10, 2013.

*Primary Examiner* — Lezah Roberts

(57) ABSTRACT

The method of the present invention is directed to the storage and dispensing of a peroxide containing tooth whitening composition. During storage and subsequent use the composition in the storage chamber must be maintained segregated from the applicator surface. This is accomplished by delivering the peroxide containing tooth whitening composition from the storage chamber through a delivery channel having a length and a cross-sectional diameter sufficient to preclude the migration of moisture and the enzyme catalase from the application surface to the storage chamber. The composition is applied to teeth by means of bristles, a sponge surface or fibrillated surface. This applicator can be used with both aqueous and non-aqueous peroxide containing tooth whitening compositions.

21 Claims, 6 Drawing Sheets

APPLICATOR AND METHOD FOR APPLYING A TOOTH WHITENING COMPOSITION

CROSS-REFERENCE TO RELATED APPLICATIONS

This is a divisional of U.S. application Ser. No. 11/403,732, filed Apr. 13, 2006, now allowed, which is a continuation of International Application No. PCT/US04/33502, filed Oct. 12, 2004, which claims priority from U.S. Provisional Application No. 60/511,020, filed Oct. 14, 2003, all of which are incorporated by reference herein in their entirety.

FIELD OF INVENTION

This invention is directed to a method of applying a tooth whitening composition to teeth and an applicator to be used in this method.

BACKGROUND

Tooth whitening products are applied in different ways. A common technique is to cast an impression of a person's teeth and provide a tray of the shape of this impression. A person then only needs to add a whitening composition to the tray and to apply the tray to his/her teeth. This is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to ones teeth. After a few treatments the teeth gradually whiten.

A problem with the latter technique is that saliva in the mouth contains the enzyme catalase. This enzyme will catalize the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative affect on the whitening composition by potentially decomposing the peroxide active ingredient. In addition if a person washes the brush each time after use moisture from the wet bristles can enter the bottle.

These problems require a better way to deliver the whitening composition to the teeth. The objective is to maintain the supply of whitening composition segregated from the general environment and from mouth saliva. This objective has to be fulfilled using a dispenser that is easy to use by a person to apply the whitening composition to his/her teeth and is gentle on the teeth and gums. Additionally in a preferred embodiment the dispenser should be readily portable.

The present invention addresses and solves these problems. Preferred dispensers are elongated and pen-like in shape. They can contain about 0.5 ml to 20 ml of a product in the body portion and they have an applicator end for applying the contained tooth whitening compositions to a person's teeth. The applicator end is constructed such that moisture and saliva components will not migrate from an applicator surface into the part of the dispenser where the whitening composition is stored. In addition the applicator components must be compatible with the whitening compositions.

BRIEF SUMMARY

This invention comprises a method for applying a tooth whitening composition to a persons teeth, and in one preferred embodiment an anhydrous tooth whitening composition. This latter composition must be maintained substantially anhydrous prior to an application to a persons teeth. In addition all compositions must be maintained free from catalase contamination during use. This requires a dispenser that is to be used for multiple treatments to maintain the stored whitening composition substantially segregated from the application surface throughout the multiple treatments. The method comprises using a dispenser having a body portion and a dispensing portion. The body portion has a cavity to contain about 0.5 ml to about 20 ml of a tooth whitening composition. At one end there is at least one aperture for the dispensing of the tooth whitening composition to an applicator. The aperture, (and collectively when there is a plurality of apertures) has a cross-sectional of area less than about 10 sq. mm, preferably less than about 5 sq. mm, and most preferably less than about 2 sq. mm. Further a channel from the body portion to the applicator surface has a length of more than about 5 mm, preferably more than about 10 mm, and most preferably more than about 15 mm. At the other end of the body portion of the dispenser is a piston to dispense the tooth whitening composition through the channel to the applicator surface. This is manually operated by a twisting motion or by a push button.

The apertures in a preferred embodiment have an associated application surface to apply the anhydrous tooth whitening composition to ones teeth. This can consist of bristles, a pad, a sponge-like surface or fibrillated surface. The size of the apertures and the length of the channel will preclude the migration of catalase and moisture into the body of the dispenser during each dispensing and subsequent to the dispensing.

DETAILED DESCRIPTION

The invention will be disclosed with regard to the preferred embodiments with reference to the drawings. This invention is directed to a method of applying a tooth whitening composition to a persons teeth from a dispenser.

It has been found that peroxide containing tooth whitening compositions are very useful in tooth whitening. These usually are applied in multiple applications. The composition in the dispenser must be maintained substantially segregated from the applicator surface from the first application through to the last application. Consequently a technique for applying the composition is needed to fulfill these requirements. There also is a further requirement that it be easy for the individual to apply it themselves. This is provided by the techniques and dispensers of this invention.

The following are useful non-aqueous whitening compositions that can be used with the present dispenser.

TABLE 1

| Component | Content |
| --- | --- |
| Non-Aqueous Hydrophilic Polymer | 5 to 85 wt % |
| Adhesive Enhancing Agent Peroxide | 0.1 to 25 wt % |
| Peroxide Whitening Agent | 0.25 to 50 wt % |
| Surfactant | 0 to 50 wt % |
| Flavor | 0.1 to 2 wt % |
| Peroxide Activator | 0 to 10 wt % |

The nonaqueous hydrophilic polymers useful in the practice of the present invention preferably provide a viscosity for the composition in the range between about 1,000 cps to 900,000 cps. This will have a moisture content of less than about 2% and preferably less than about 1%.

A preferred nonaqueous liquid hydrophilic polymer vehicles suitable for use in the practice of the present invention includes polyethylene glycols, that is, nonionic polymers of ethylene oxide having the general formula:

$$HOCH_2(CH_2OCH_2)_nOH$$

wherein n represents the average number of oxyethylene groups. Polyethylene glycols available from Dow Chemical are designated by a number such as 200, 300, 400, 600, 2000 which represents the approximate average molecular weight of the polymer. Polyethylene glycols 200, 300, 400 and 600 are clear viscous liquids at room temperature, and are preferred for use in the practice of the present invention.

A second preferred nonaqueous liquid hydrophilic polymer used to prepare the composition of the present invention is comprised of a water soluble, nonionic block copolymer of ethylene oxide and propylene oxide of the formula:

$$HO(C_2H_4O)_a(C_3H_6O)_b(C_2H_4O)_cH$$

The block copolymer is preferably chosen (with respect to a, b and c) such that the ethylene oxide constituent comprises from about 65 to about 75% by weight, of said copolymer molecule and the copolymer has an average molecular weight of from about 2,000 to about 15,000, with the copolymer being present in the liquid tooth whitening composition in such concentration that the composition is liquid at room temperatures (23° C.).

A particularly desirable block copolymer for use in the practice of the present invention is available commercially from BASF and designated Pluraflo L1220 which has an average molecular weight of about 9,800. The hydrophilic poly(ethylene oxide) block averages about 65% by weight of the polymer.

Adhesion enhancing agents are used in the compositions of the present invention to enhance the adhesive properties of the anhydrous hydrophilic polymers and include inorganic materials as well as organic natural and synthetic polymers. Inorganic materials include amorphous silica compounds which function as thickening agents include colloidal silica compounds available under trademarks such as Cab-o-sil fumed silica manufactured by Cabot Corporation and distributed by Lenape Chemical, Bound Brook, NJ; Zeodent 165 from J.M. Huber Chemicals Division, Havre de Grace, Md. 21078; and Sylox 15 also known as Sylodent 15, available from Davison Chemical Division of W.R. Grace Corporation, Baltimore, Md. 21203.

Organic polymers useful as adhesion enhancing agents useful in the practice of the present invention include hydrophilic polymers such as carbomers such as carboxymethylene polymers such as acrylic acid polymers, and acrylic acid copolymers. Carboxypolymethylene is a slightly acidic vinyl polymer with active carboxyl groups. A carboxypolymethylene preferred for use in the practice of the present invention is a copolymer of acrylic acid cross linked with approximately 0.75% to approximately 1.5% polyallyl sucrose that is sold under the trade designation Carbopol 934, 974 by B.F. Goodrich.

Hydrophobic organic materials are also useful as adhesion enhancing agents in the practice of the present invention include hydrophobic materials such as waxes such as bees wax, mineral oil, plastigel, (a blend of mineral oil and polyethylene), petrolatum, white petrolatum, versagel (blend of liquid paraffin, butene/ethylene/styrene hydrogenated copolymer) acrylate and vinyl acetate polymers and copolymers, polyethylene waxes, silicone polymers such as dimethicone, silicone elastomers, organosiloxane resins, silicone gums and polyvinyl pyrrolidone/vinyl acetate copolymers.

Anhydrous whitening agents useful in the practice of the present invention include anhydrous peroxide containing compounds such as urea peroxide, sodium percarbonate, sodium perborate and PVP-$H_2O_2$ complexes (hereinafter "PVP-$H_2O_2$"). PVP-$H_2O_2$ both linear and cross linked complexes are known to the art and are disclosed in U.S. Pat. No. 3,376,110 and U.S. Pat. No. 3,480,557 and have been used in compositions for treating acne vulgaris (U.S. Pat. No. 5,122,370). PVP-$H_2O_2$ complexes are disclosed in U.S. Pat. No. 5,122,370. PVP-$H_2O_2$ is stable in an anhydrous environment. By exposure to aqueous environments, as in the oral cavity, the whitening agent dissociates into individual species (PVP polymer and $H_2O_2$). The PVP-$H_2O_2$ complex is generally comprised of about 80% by weight polyvinyl pyrrolidone and 20% by weight $H_2O_2$.

Nonionic surfactants which are compatible with peroxide compounds serve as a solubilizing, dispersing, emulsifing and wetting agents and are especially effective to solubilize a flavor if included in the liquid whitening composition. A particularly useful nonionic surfactant is a water soluble polyoxyethylene monoester of sorbitol with a C10 to C18 fatty acid, marketed commercial under the Tween trademark. The Tween surfactants are mixtures of C10 to C18 fatty acid esters of sorbitol (and sorbitol anhydrides), consisting predominately of the monoester, condensed with about 10-30, preferably about 20, moles of ethyleneoxide. The fatty acid (aliphatic hydrocarbonyl monocarboxylic acid) may be saturated or unsaturated, e.g., lauric, palmitic, stearic, oleic acids. Polysorbate 20 (e.g., Tween 20) is especially preferred and is commonly referred to as polyoxyethylene (20) sorbitan monolaurate. The nonionic surfactant constitutes about 0 to 50% by weight and preferably 0.5 to 40% by weight of the liquid composition.

Flavoring agents that are useful include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is incorporated in the whitening liquid composition of the present invention at a concentration of about 0.1 to about 2% by weight and preferably about 0.1 to about 0.5% by weight. A sweetening material may also be employed as a complement to the flavoring material. Suitable sweetening agents are water soluble and include sodium saccharin, sodium cyclamate, xylitol, perillartien, D-tryptophan, aspartame, dihydrochalcones and the like.

Peroxide decomposition activators such as sodium bicarbonate, sodium carbonate, manganese gluconate may be incorporated in the liquid whitening gel composition of the present invention. The activator is relatively nonactive with the peroxide whitening agent when present in the stored nonaqueous liquid composition due to the anhydrous compositions. The activator functions to react with the peroxide to release oxygen when the liquid whitening composition applied to the teeth is contacted with saliva in the oral cavity.

An enhancement of the above compositions is to add a silicone adhesive agents. This will aid in holding the peroxide whitening agent onto tooth surfaces. This is formed by condensing a silicone resin and an organosiloxane such as polydiorgano siloxane. Useful silicone adhesive agents are available from the Dow Corning Company under the brand name BIO-SPA. These can be present in a content of about 1 to 80 wt present.

Suitable aqueous whitening composition are set out in Table 2. However other aqueous whitening compositions can be used.

TABLE 2

| Carbopol Polymer | 0.1 to 4 wt % |
| Polyethylene glycol | 2 to 30 wt % |
| Antioxidant | .01 to .1 wt % |
| Humectant | 0 to 50 wt % |
| Thickener | 0 to 5 wt % |
| Hydrogen peroxide | 1 to 35 wt % |
| Monobasic sodium phosphate | 0 to 5 wt % |
| Phosphoric Acid | 0 to 1 wt % |
| Flavor | .1 to 1 wt % |
| Saccharin | .01 to 1 wt % |
| Purified water | to 100 wt % |

The Carbopol polymer, polyethylene glycol, flavors and saccharin been described above with regard to the nonaqueous tooth whitening compositions.

A preferred useful antioxidant is butylated hydroxyl toluene. Other useful antioxidants include nordihydroguararetic acid, propyl gallate and trihydroxy butrophenone.

A preferred humectant is glycerin. Other useful humectants include sorbitol and polytheylene glycol in a molecular weight range of 200 to 1000. Mixtures of humectants also can be used.

A preferred thickner is xanthan gum. However a range of organic natural and synthetic thickness can be used. These include carrageenan, starch, polyvinylpyrrolidone, and cellulose compounds such as hydroxypropyl menthyl cellulose, hydroxyethyl cellulose, hydroxyethylpropyl cellulose and hydroxybutyl methyl cellulose.

Hydrogen peroxide is a preferred whitening agent and preferably is added as a 35% solution of hydrogen peroxide in the peralkalai form. However it can be used at other concentrations and can be used in a form where hydrogen peroxide is released during use. Some such peroxides in another form are discussed above.

Phosphoric acid is the preferred acid added to adjust the pH of the composition. However a range of equivalent organic and inorganic acids can be used. These include sulfuric, hydrochloric, alginic, citric, succinic, lactic and tartaric acids and their salts. Included are salts of these acids with a preferred phosphoric acid salt being monobasic sodium phosphate.

The compositions can be made by mixing the components together in essentially any order. However one technique is for the components other than the polymers and thickeners, and water for the aqueous compositions, be admixed together and then the polymers and thickeners added. Water would be added to the aqueous to achieve the desired viscosity. An objective is for the production of a uniform whitening composition.

Figure 1:
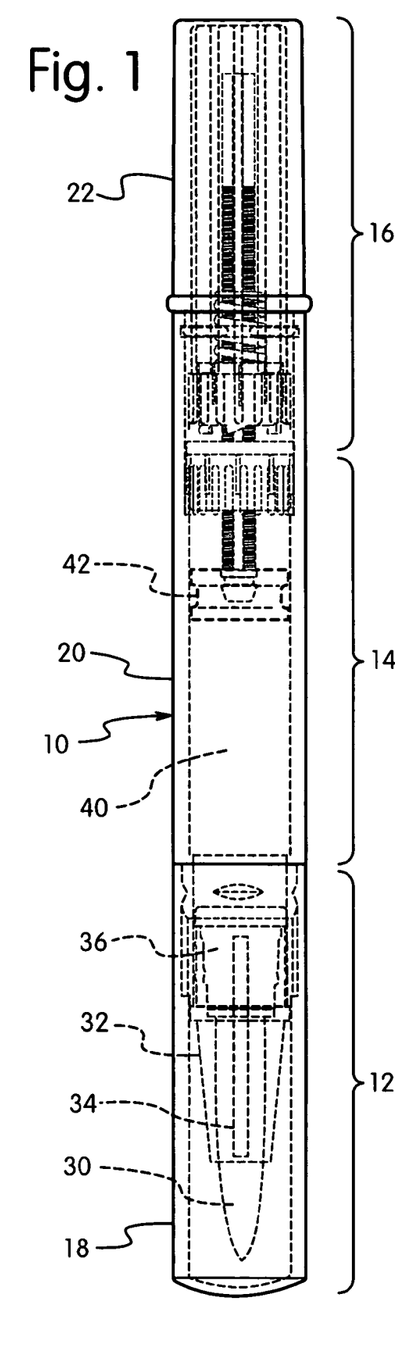
FIG. 1 is an elevational view of a dispenser for a tooth whitening composition.
Figure 2:
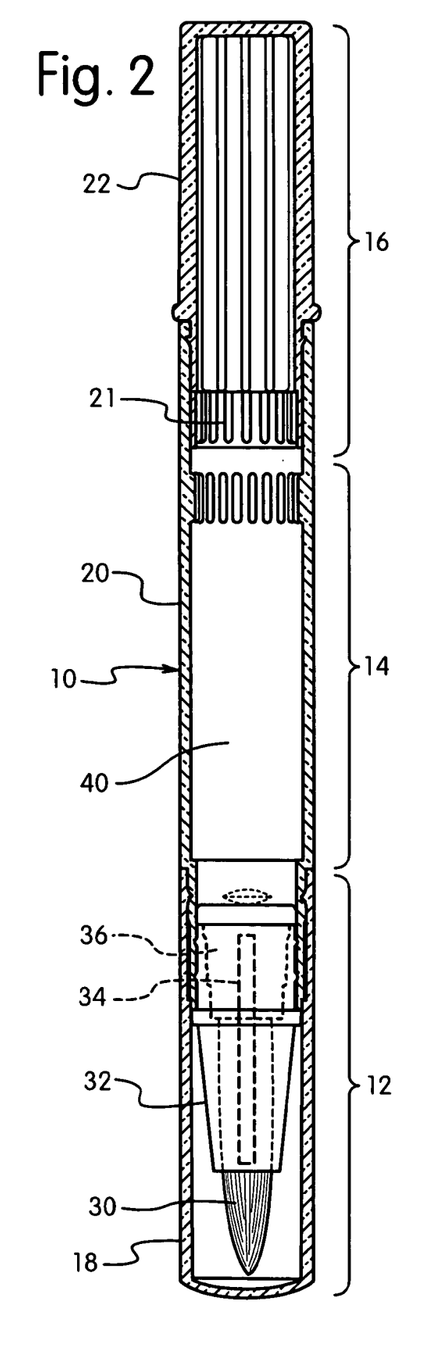
FIG. 2 is an elevational view of the dispenser of FIG. 1 in a vertical section.

The dispenser 10 is shown as a complete unit in FIGS. 1 and 2. The dispenser is comprised of three sections. These are an applicator section 12, a whitening product storage section 14 and a dispenser drive section 16. The applicator section is comprised of an overcap 18, an applicator surface 30, an applicator surface holder 32, an applicator mounting unit 36 and a delivery channel 34. The whitening product in product chamber 40 is delivered to the applicator surface through delivery channel 34. A tubular wall 20 forms the product chamber 40. Piston 42 forms the upper wall of product chamber 40.

The dispenser drive section 16 is comprised of the mechanism to advance piston 42 downward in whitening product chamber 40. This dispenser drive section is shown in more detail in FIG. 5. Rotating unit 22 will rotate while tubular wall 20 of the whitening product chamber is stationary.

Figure 3:
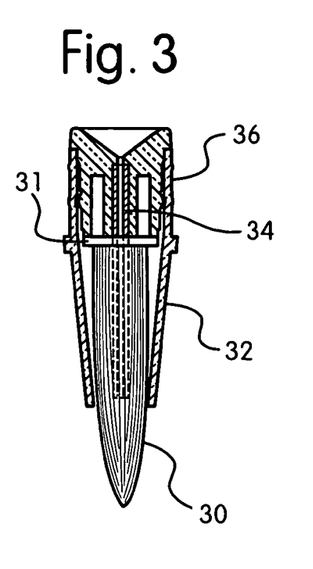
FIG. 3 is an exploded view of the applicator tip of the dispenser.
Figure 4:
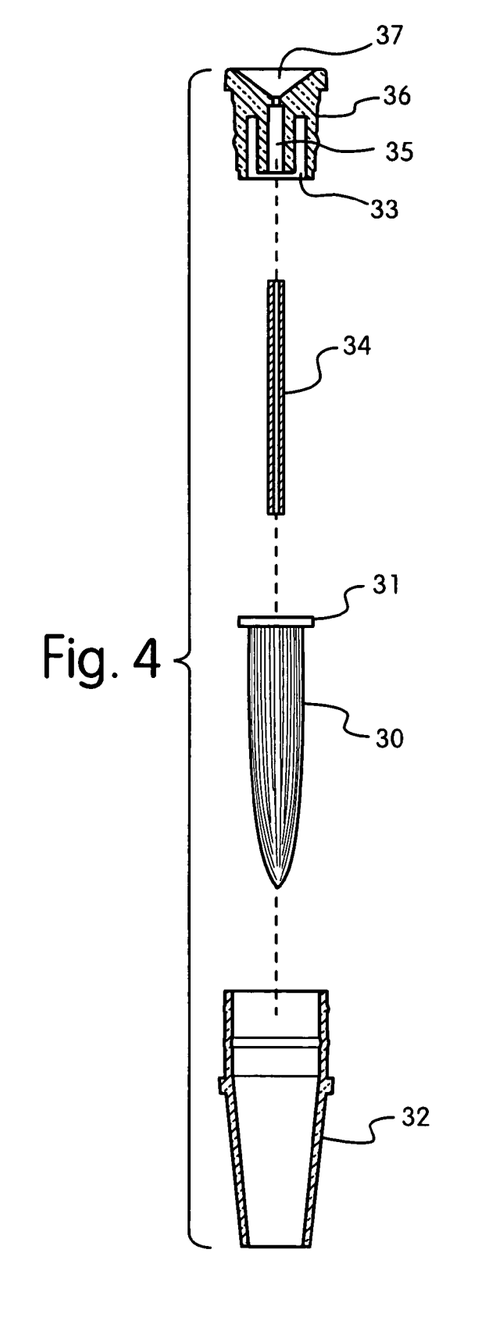
FIG. 4 is an elevational view in a vertical section of the applicator tip assembled.

FIGS. 3 and 4 show the applicator section 12 in more detail. The applicator surface 30 is shown here as a bundle of bristles in holder 32. The bristles are inserted into bristle holder 32 with flange 31 of the bristles held in recess 33. The delivery channel 34 is held by friction in the center passage 35 of the applicator mounting unit 36. Whitening product will flow through passage 37 of the applicator mounting unit 36, into delivery channel 34 and then onto the applicator surface 30. The applicator section 12 is shown prior to assembly in FIG. 4.

Figure 5:
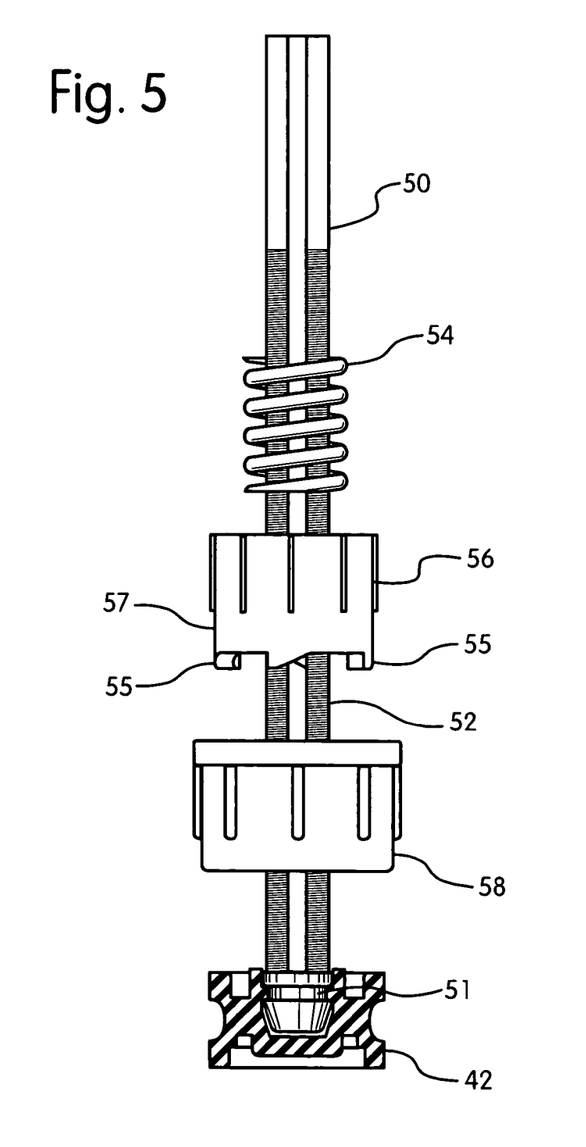
FIG. 5 is an elevational view of the drive mechanism of the dispenser.

FIG. 5 shows the mechanism of drive section 16. At a lower end is piston 42 which is attached to piston rod 50. This piston rod 50 has threads 52 over a substantial part of its length. Stationary unit 58 is held in place in whitening product section 20 by an interlocking of ribs 56 and recesses 21 on product chamber wall 20 in FIG. 2. Rotary unit 57 fits into stationary unit 58 and has rotation limiting cams 55 and on a lower surface. These cams 55 interact with a cooperating cam surface in stationary unit 58 to limit rotation of piston rod 50 to only one direction to only move piston 42 downward. The piston cannot be retracted upward since this would draw product in delivery channel 34 towards and/or into the product chamber 40. This could cause contamination of product in product chamber 40. The piston is held in recess 51 of the piston rod 50. A spring 54 causes rotating unit 57 to stay mounted within stationary unit 58.

Figure 6:
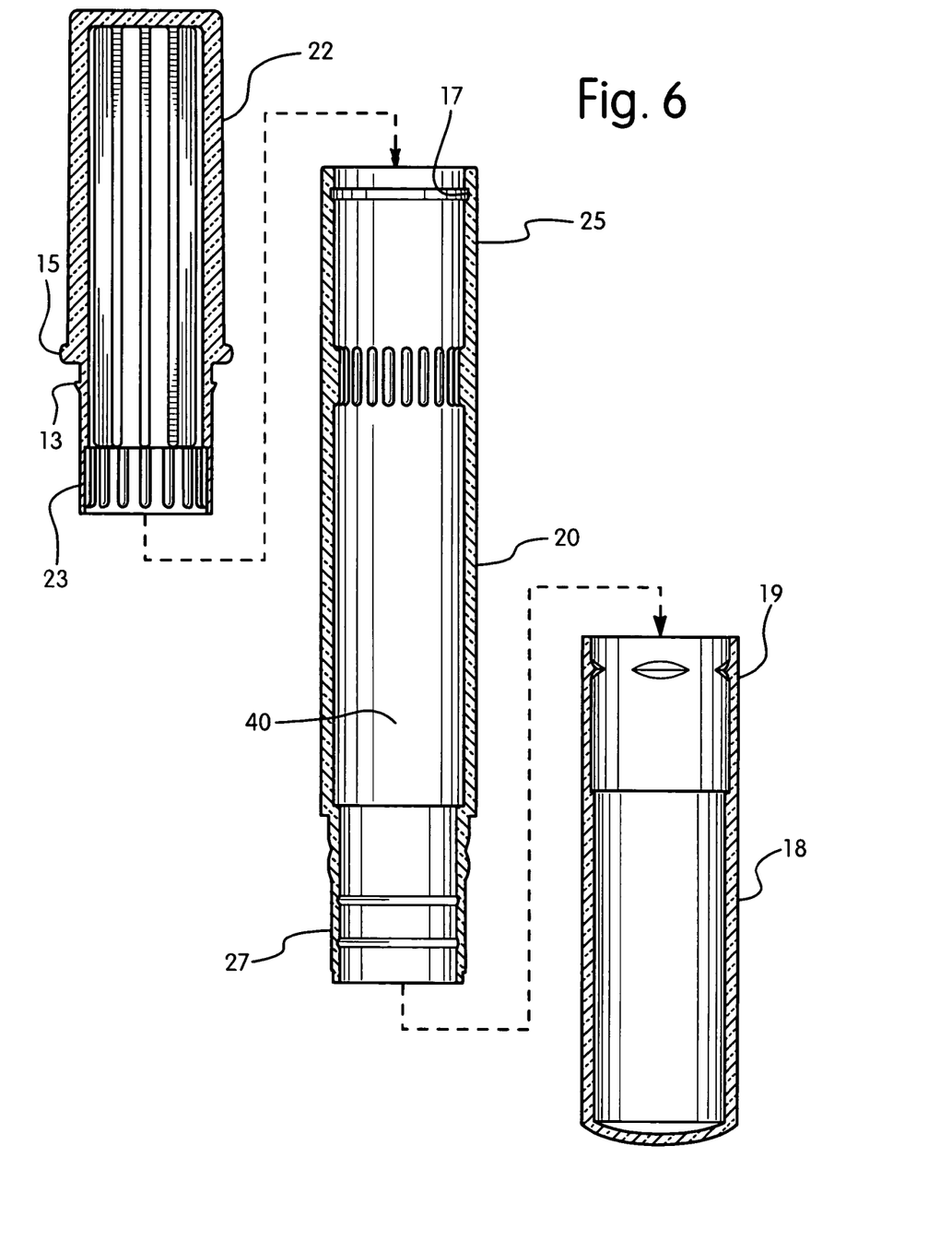
FIG. 6 is an exploded view of the dispenser casing.

FIG. 6 shows the exterior parts of the dispenser in a exploded view. Shaft 23 of rotating unit 22 fits into and rotates within whitening product section 14. It is held in place on the lower end of the product section tubular wall 20 by projection 13 and recess 17. Overcap 18 fits onto end section 25 of the composition containing unit 40.

Figure 7:
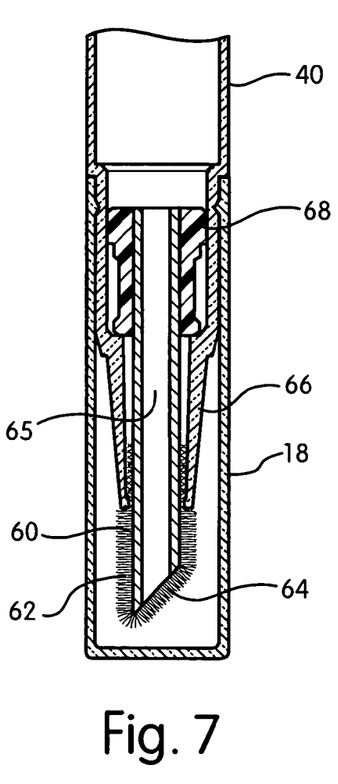
FIG. 7 is an elevational view of an applicator tip with a fibrillated surface in a casing in vertical section.
Figure 8:
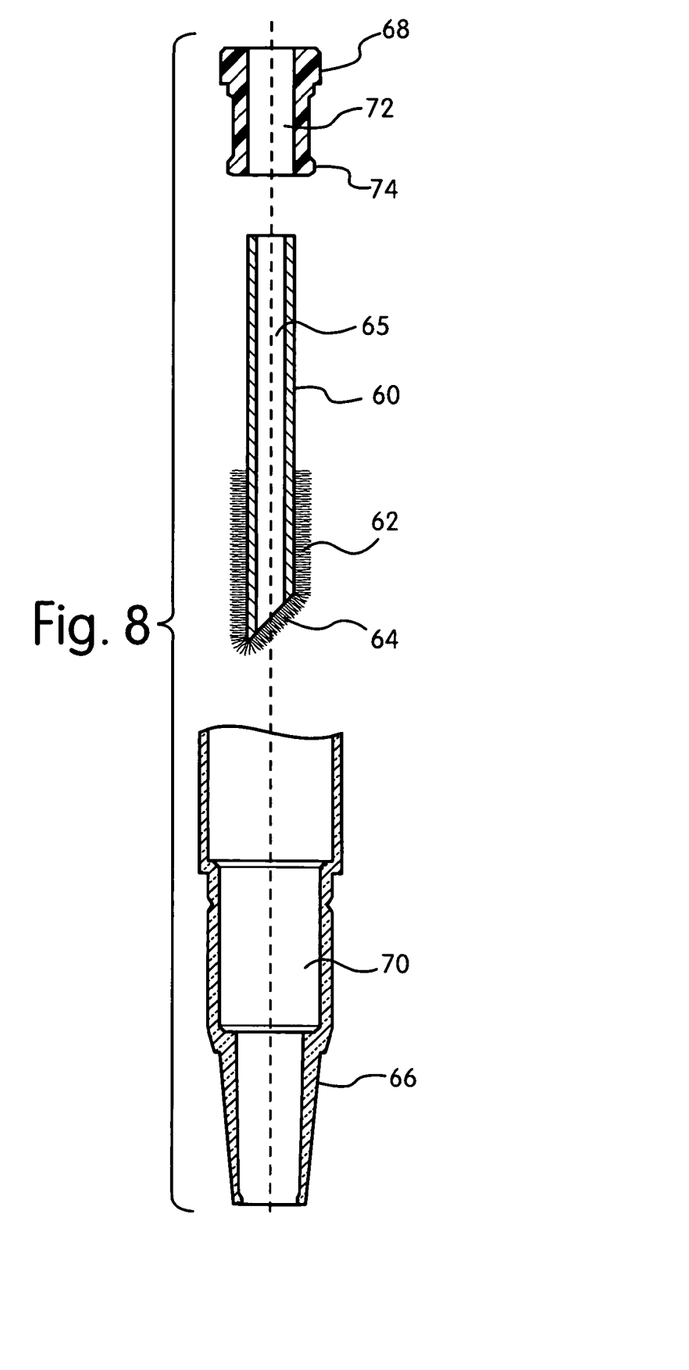
FIG. 8 is an exploded view of the applicator tip of FIG. 7

FIG. 7 shows an applicator tip with a fibrillated surface The applicator tip is comprised of channel 60 having a cross-section 65 which receives the peroxide containing tooth whitening composition from storage chamber 40. Fibrillated surface 62 is the application surface to apply the composition to the teeth. The peroxide tooth whitening composition flows through opening 64 of the channel 60. Applicator surface holder 66 holds channel 60 and is in turn held in place by applicator mounting unit 68. FIG. 8 is an exploded view of the applicator tip of FIG. 7. Additionally shown in this view is a chamber 70 on the applicator surface holder channel 72 of the applicator mounting unit 68. Flange 74 holds the applicator surface holder 66 in applicator mounting unit 68.

Figure 9:
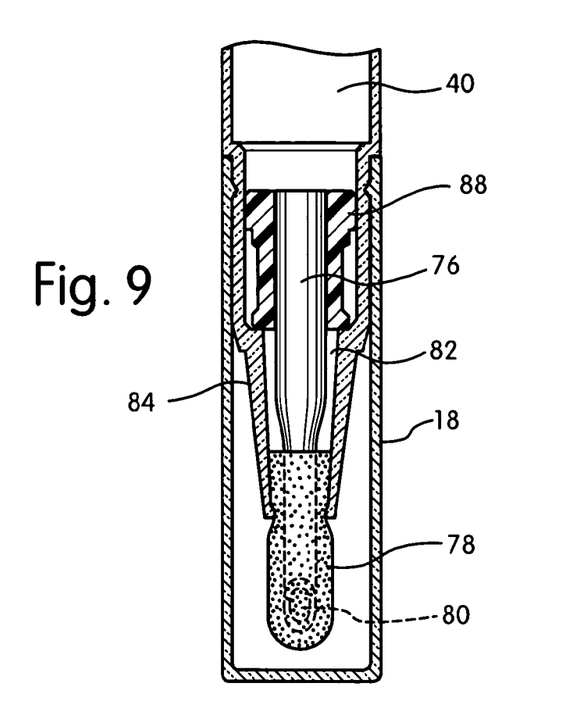
FIG. 9 is an elevational view of an applicator tip with a sponge-like surface in a casing in a vertical section.
Figure 10:
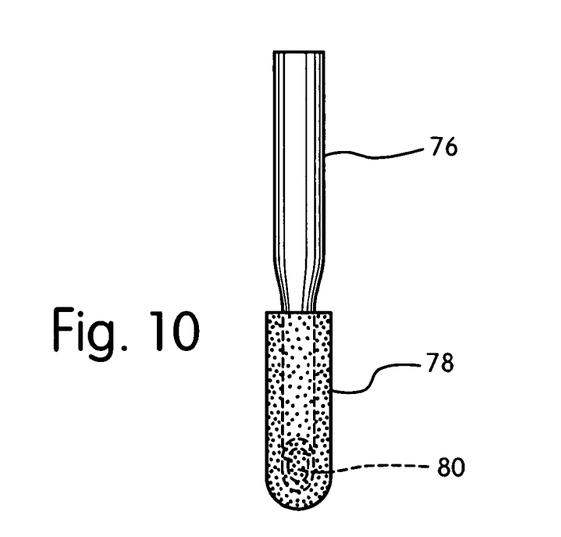
FIG. 10 is an elevational view of the applicator tip with a sponge-like surface of FIG. 9.

FIGS. 9 and 10 show a sponge-like applicator surface. Delivery channel 76 has a porous sponge-like surface 78 on the applicator end. This applicator end has an aperture 80 for the delivery of the peroxide containing tooth whitening composition. An overcap 18 covers the applicator tip end. Shown are applicator tip holder 84 and applicator mounting unit 88. The parts of this applicator tip are shown in more detail in FIGS. 10 to 13.

The chamber 40 will contain about 0.5 ml to about 20 ml of the tooth whitening composition. The delivery channels 34, 60, 76 will maintain the product in chamber 40 segregated from the applicator surface 30, 64, 78. This segregation primarily is affected by the length and internal diameter of delivery channel 34. This delivery channel should have a length of more than about 5 mm, and preferably more than about 10 mm, and most preferably more than about 15 mm. The internal diameter should be less than of about 4 mm and preferably less than about 2 mm. When there are a plurality of channels the additive diameter of all channels should be less than about 4 mm and preferably less than about 2 mm. The cross-sectional area of the channel should be less than 15 sq. mm, and preferably less than about 7 sq. mm. This is the cross-sectional area of a single channel or if more than one channel, cross-sectional diameter of the total number of channels.

The dispenser can be made out of any moldable plastics. Moldable thermoplastics are preferred. Suitable plastics include polymers and copolymers of ethylene, propylene, butadiene, vinyl compounds and polyesters such as polyethylene terephthalate. However the chosen plastics must be compatible with peroxide containing compositions and should no degrade such compositions. The bristles can be of any common bristle material such as nylon. The sponge-like materials can be of any common foam material such as urethane foams. The fibrillated surfaces will be comprised various thermoplastics. These are all known materials.

The applicator for the whitening composition can be any surface that can apply a viscous substance onto the hard surface of teeth. This can include a bristle surface, a sponge surface or a fibrillated surface. In the use of a bristle surface the delivery channel will deliver the composition to near the ends of the bristles. Usually there will be a single delivery channel. For sponge and fibrillated surfaces there usually will be plurality of smaller diameter channels so as to more uniformly distribute the composition onto a persons teeth. A fibrillated surface is an essentially planar surface that has a plurality of protruding fibrils up to about 3 millimeter in length. Such a fibrillated surface provides a mini-brush surface.

The viscosity is measured using a Brookfield Model DV II viscometer with spindle E. The sample is centered about 0.6 cm to 1.25 cm below the spindle tip. The viscometer motor is started which starts spindle rotation. The helipath switch on lowers the spindle. When the spindle penetrates the sample the pen on a recorder senses the different force on the spindle. The spindle is monitored for 1.5 minutes. The viscosity is calculated from a line tangent to the Y-slope and another averaging the X-slope an the intersection of these tangent lines.

What is claimed is:

1. A dispenser for a peroxide containing tooth whitening composition comprising:
   a housing comprising a reservoir sealed at one end and having a channel at another end, wherein the channel has a length;
   an applicator comprising an aperture provided at the end of the channel, wherein the aperture has a cross-sectional area, and wherein the length of the channel and the cross-sectional area are sized and configured to prevent the migration of substances from the applicator into the reservoir between applications:
   the peroxide containing tooth whitening composition in the reservoir to be dispensed through the channel and the aperture to an applicator surface, and
   a drive mechanism disposed within the housing, the drive mechanism comprising:
      a moveable piston attached to a threaded piston rod;
      a stationary unit; and
      a rotary unit having a surface comprising rotation limiting cams that directly engage and interact with a cooperating cam surface on said stationary unit, wherein the threaded piston rod extends through the stationary unit and the rotary unit;
   wherein the interaction between the rotation limiting cams of the rotary unit and the cooperating cam surface of the stationary unit limits rotation of the threaded piston rod to only one direction that moves the movable piston toward the another end, and wherein the seal at the one end is formed by the moveable piston, whereby when the moveable piston is moved toward the another end, the peroxide containing tooth whitening composition flows through the channel and the aperture to the applicator surface for application onto at least one tooth.

2. The dispenser as in claim 1 wherein the aperture has a cross-sectional area of less than about 10 sq. mm.

3. The dispenser as in claim 1 wherein the channel has a length of more than about 5 mm.

4. The dispenser as in claim 3 wherein the channel has a length of more than about 10 mm.

5. The dispenser as in claim 1 wherein the channel has a diameter of less than about 4 mm.

6. The dispenser as in claim 1 wherein the tooth whitening composition has a moisture content of less than about 2 percent by weight.

7. The dispenser as in claim 6 wherein the moisture content of the peroxide containing tooth whitening composition is less than about 1 percent by weight.

8. The dispenser as in claim 1 wherein the peroxide content of the peroxide containing whitening composition is about 0.25% to about 50% by weight.

9. The dispenser as in claim 8 wherein the peroxide content of the peroxide containing tooth whitening composition is about 1% to about 35% by weight.

10. The dispenser as in claim 1 wherein the viscosity of the peroxide containing tooth whitening composition is about 1000 cps to about 900,000 cps.

11. The dispenser as in claim 10 wherein the viscosity of the peroxide containing tooth whitening composition is about 10,000 cps to about 500,000 cps.

12. The dispenser as in claim 1 wherein the applicator comprises a plurality of bristles surrounding the aperture.

13. The dispenser as in claim 1 wherein the aperture comprises a plurality of apertures having a combined surface area of less than about 10 sq. mm.

14. The dispenser as in claim 1 wherein the applicator comprises a sponge.

15. The dispenser as in claim 1 wherein the applicator comprises a fibrillated surface.

16. The dispenser as in claim 1 wherein the tooth whitening composition is a non-aqueous composition.

17. The dispenser as in claim 16 wherein the non-aqueous composition is comprised of the following formulations:

| Component | Content |
| --- | --- |
| Non-Aqueous Hydrophilic Polymer | 5 to 85 wt % |
| Adhesive Enhancing Agent Peroxide | 0.1 to 25 wt % |
| Peroxide Whitening Agent | 0.25 to 50 wt % |
| Surfactant | 0 to 50 wt % |
| Flavor | 0.1 to 2 wt % |
| Peroxide Activator | 0 to 10 wt %. |

18. The dispenser as in claim 1 wherein the tooth whitening composition is an aqueous composition.

19. The dispenser as in claim 18 wherein the tooth whitening composition is comprised of the following formulations:

| | |
| --- | --- |
| Carbopol Polymer | 0.1 to 4 wt % |
| Polyethylene glycol | 2 to 30 wt % |
| Antioxidant | .01 to .1 wt % |
| Humectant | 0 to 50 wt % |
| Thickener | 0. to 5 wt % |
| Hydrogen peroxide | 1 to 35 wt % |
| Acid salt | 0 to 5 wt % |
| Acid pH adjustment | 0 to 1 wt % |
| Flavor | .1 to 1 wt % |
| Saccharin | .01 to 1 wt % |
| Purified water | To 100 wt %. |

20. The dispenser as in claim 1 wherein the piston is not rotatable.

21. The dispenser as in claim 20 wherein the piston is movable along a longitudinal axis of the housing and at least partially within the drive mechanism.

* * * * *